(12) United States Patent
Lee et al.

(10) Patent No.: US 8,889,376 B2
(45) Date of Patent: Nov. 18, 2014

(54) FUSION PROTEIN BINDING SPECIFICALLY TO CONSTANT REGION OF ANTIBODY, METHOD OF PREPARING THE FUSION PROTEIN, AND METHOD OF ISOLATING ANTIBODY USING THE FUSION PROTEIN

(75) Inventors: Jae-Il Lee, Yongin-si (KR); Young-Sun Lee, Yongin-si (KR); Tae-Soo Lee, Seoul (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 0 days.

(21) Appl. No.: 13/508,002

(22) PCT Filed: Aug. 6, 2010

(86) PCT No.: PCT/KR2010/005159
§ 371 (c)(1),
(2), (4) Date: Jul. 23, 2012

(87) PCT Pub. No.: WO2011/055897
PCT Pub. Date: May 12, 2011

(65) Prior Publication Data
US 2012/0283408 A1    Nov. 8, 2012

(30) Foreign Application Priority Data
Nov. 3, 2009    (KR) .................. 10-2009-0105490

(51) Int. Cl.
| | | |
|---|---|---|
| *C07K 14/47* | (2006.01) | |
| *C12N 15/62* | (2006.01) | |
| *C12N 15/63* | (2006.01) | |
| *C07K 16/06* | (2006.01) | |
| *C07K 16/32* | (2006.01) | |

(52) U.S. Cl.
CPC .............. *C07K 16/065* (2013.01); *C07K 16/32* (2013.01); *C07K 2319/00* (2013.01); *C07K 2319/70* (2013.01)
USPC ....... 435/69.7; 530/300; 530/387.1; 530/412; 530/413; 536/23.4; 435/252.3

(58) Field of Classification Search
CPC ............. C07K 2319/00; C07K 16/065; C07K 2319/70
USPC ...................... 530/402, 300, 387.1, 412, 413; 536/23.4; 435/252.3, 69.7
See application file for complete search history.

(56) References Cited

U.S. PATENT DOCUMENTS

| | | |
|---|---|---|
| 5,709,859 A | 1/1998 | Aruffo et al. |
| 2007/0072307 A1 | 3/2007 | Godavarti et al. |
| 2009/0171072 A1 | 7/2009 | Alfonso et al. |

OTHER PUBLICATIONS

Extended Search Report from the International Searching Authority in corresponding PCT Application No. PCT/KR2010/005159 (Oct. 22, 2013).
"Ubiquitin Fusion System for Recombinant Peptide Expression and Purification: Application to the Cytoplasmic Domain of Syndecan-4," *Bulletin of the Korean Chemical Society*, 2007, vol. 28, No. 9, pp. 1549-1552.
Yang et al., "Hexamer peptide affinity resins that bind the Fc region of human immunoglobulin G," *Journal of Peptide Research*, Blackwell Publishing Ltd., Oxford; GB, 2005, vol. 66, No. Suppl 1, 120-137.
International Search Report from the International Searching Authority in corresponding PCT Application No. PCT/KR2010/005159 (Jul. 20, 2011).
Ehrlich et al., "Identification of Model Peptides as Affinity Ligands for the Purification of Humanized Monoclonal Antibodies by Means of Phage Display," *Journal of Biochemical and Biophysical Methods*, 2001, 443-454, 49.
Roque et al., "Antibodies and Genetically Engineered Related Molecules: Productioin and Purification," *Biotechnology Progress*, 2004, 639-654, 20-3.
Yang, Haiou, Paper for Doctor of Philosophy degree, Titled: "Fc-Binding Hexamer Peptide Ligands for Immunoglobulin Purification," Aug. 2008, 20-22, 52, 208-212, Table 3-1, Department of Chemical and Biomolecular Engineering, North Carolina State University.
Yang et al., "Purification of Human Immunoglobulin G via Fc-specific Small Peptide Ligand Affinity Chromatography," *Journal of Chromatography A*, 2009, 910-918, 1216.

*Primary Examiner* — Prema Mertz
(74) *Attorney, Agent, or Firm* — Leydig, Voit & Mayer, Ltd.

(57) ABSTRACT

A fusion protein that includes a polypeptide binding specifically to a constant region of an antibody and a stabilization protein linked to a terminus of the polypeptide, a polynucleotide encoding the fusion protein, a cell including the polynucleotide, a method of preparing the fusion protein, and a method of isolating an antibody by using the fusion protein.

12 Claims, 3 Drawing Sheets

```
                            SEQUENCE LISTING

<160> NUMBER OF SEQ ID NOS: 12

<210> SEQ ID NO 1
<211> LENGTH: 76
<212> TYPE: PRT
<213> ORGANISM: Homo sapiens

<400> SEQUENCE: 1

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly
65                  70                  75

<210> SEQ ID NO 2
<211> LENGTH: 76
<212> TYPE: PRT
<213> ORGANISM: Homo sapiens

<400> SEQUENCE: 2

Met Gln Ile Phe Val Arg Thr Leu Thr Gly Arg Thr Ile Thr Leu Glu
1               5                   10                  15

Val Glu Pro Ser Asp Thr Ile Glu Asn Val Arg Ala Arg Ile Gln Asp
            20                  25                  30

Arg Glu Gly Ile Pro Pro Asp Gln Gln Arg Leu Ile Phe Ala Gly Arg
        35                  40                  45

Gln Leu Glu Asp Gly Arg Thr Leu Ser Asp Tyr Asn Ile Gln Arg Glu
    50                  55                  60

Ser Thr Leu His Leu Val Leu Arg Leu Arg Gly Gly
65                  70                  75

<210> SEQ ID NO 3
<211> LENGTH: 12
<212> TYPE: PRT
<213> ORGANISM: Artificial Sequence
<220> FEATURE:
<223> OTHER INFORMATION: polypeptide binding specifically to constant
      region of antibody

<400> SEQUENCE: 3
```

Glu Pro Ile His Arg Ser Thr Leu Thr Ala Leu Leu
1               5                   10

<210> SEQ ID NO 4
<211> LENGTH: 12
<212> TYPE: PRT
<213> ORGANISM: Artificial Sequence
<220> FEATURE:
<223> OTHER INFORMATION: polypeptide binding specifically to constant
      region of antibody

<400> SEQUENCE: 4

Glu Ile Leu Asn Met Pro Asn Leu Asn Glu Glu Gln
1               5                   10

<210> SEQ ID NO 5
<211> LENGTH: 12
<212> TYPE: PRT
<213> ORGANISM: Artificial Sequence
<220> FEATURE:
<223> OTHER INFORMATION: polypeptide binding specifically to constant
      region of antibody

<400> SEQUENCE: 5

Glu Ile Leu His Leu Pro Asn Leu Asn Glu Glu Gln
1               5                   10

<210> SEQ ID NO 6
<211> LENGTH: 12
<212> TYPE: PRT
<213> ORGANISM: Artificial Sequence
<220> FEATURE:
<223> OTHER INFORMATION: polypeptide binding specifically to constant
      region of antibody

<400> SEQUENCE: 6

Glu Ile Leu His Leu Pro Asn Leu Thr Glu Glu Gln
1               5                   10

<210> SEQ ID NO 7
<211> LENGTH: 231
<212> TYPE: DNA
<213> ORGANISM: Homo sapiens

<400> SEQUENCE: 7
atgcagattt tcgtgaaaac ccttacgggg aagaccatca ccctcgaggt tgaaccctcg      60
gatacgatag aaaatgtaaa ggccaagatc caggataagg aaggaattcc tcctgatcag     120
cagagactga tctttgctgg caagcagctg gaagatggag tactttgtc tgactacaat      180 attcaaaagg agtctactct tcatcttgtg ttgagacttc gtggtggtta a              231

<210> SEQ ID NO 8
<211> LENGTH: 231
<212> TYPE: DNA
<213> ORGANISM: Homo sapiens

<400> SEQUENCE: 8
atgcagattt tcgtgagaac ccttacgggg aggaccatca ccctcgaagt tgaaccctcg      60
gatacgatag aaaatgtaag ggccagaatc caggataggg aaggaatacc tcctgatcag     120
cagagactga tctttgctgg caggcagctg gaagatggac gtactttgtc tgactacaat     180
attcaaaggg agtctactct tcatcttgtg ttgagacttc gtggtggtta a              231

<210> SEQ ID NO 9

```
<211> LENGTH: 363
<212> TYPE: DNA
<213> ORGANISM: Artificial Sequence
<220> FEATURE:
<223> OTHER INFORMATION: DNA fragment encoding fusion protein binding
      specifically to constant region of antibody

<400> SEQUENCE: 9
atgagaggat cgcatcacca tcaccatcac gattacgata tcccaacgac cgaaaacctg      60
tattttcagg gatctgaacc aatccatcgt ag

-continued

```
<223> OTHER INFORMATION: DNA fragment encoding fusion protein binding
      specifically to constant region of antibody

<400> SEQUENCE: 12
atgagaggat cgcatcacca tcaccatcac gattacgata tcccaacgac cgaaaacctg     60
tattttcagg gatctgaaat tttacattta cctaacttaa ctgaagaaca aggtagtagc    120
ggcatgcaga ttttcgtgag aacccttacg gggaggacca tcaccctcga agttgaaccc    180
tcggatacga tagaaaatgt aagggccaga atccaggata gggaaggaat acctcctgat    240
cagcagagac tgatctttgc tggcaggcag ctggaagatg gacgtacttt gtctgactac    300
aatattcaaa gggagtctac tcttcatctt gtgttgagac ttcgtggtgc tggatcctgc    360
taa                                                                  363
```

FUSION PROTEIN BINDING SPECIFICALLY TO CONSTANT REGION OF ANTIBODY, METHOD OF PREPARING THE FUSION PROTEIN, AND METHOD OF ISOLATING ANTIBODY USING THE FUSION PROTEIN

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 6,646 Byte ASCII (Text) file named "710183_ST25.txt," created on Jul. 23, 2012.

CROSS-REFERENCE TO RELATED APPLICATIONS

This application claims the benefit of Korean Patent Application No. 10-2009-0105490, filed on Nov. 3, 2009, in the Korean Intellectual Property Office, the disclosure of which is incorporated herein in its entirety by reference.

BACKGROUND

1. Field

The present disclosure relates to a fusion protein that includes a polypeptide binding specifically to a constant region of an antibody and a stabilization protein linked to a terminal of the polypeptide, a polynucleotide encoding the fusion protein, a cell including the polynucleotide, a method of preparing the fusion protein, and a method of isolating an antibody by using the fusion protein.

2. Description of the Related Art

Affinity chromatography is a method of isolating a target material by specific binding characteristics with respect to the target material. Examples of the affinity chromatography include protein A affinity chromatography using a protein A having affinity with an immunoglobulin G. The protein A affinity chromatography is wildly used to mass-produce antibodies because 95% or more of high isolation purity can be achieved using a single process only. The protein A affinity chromatography uses selective affinity between a protein A, which is a cell surface protein found in Staphylococcus aureus, and a constant region of immunoglobulin, and is generally used to isolate antibodies.

When conventional protein A affinity chromatography columns are repeatedly used, ligands are likely to leak out, and contaminants generated when the protein A is formed retain an affinity with IgG and continue to form a complex. Thus, it may not be easy to remove the contaminants from an isolated antibody. In addition, the protein A, which is a bacteria protein, needs to be removed because it may cause undesired immune reactions. When antibodies are industrially produced, the manufacturing costs are greatly dependent on the costs for antibody isolation and purification. Since the protein A affinity chromatography is very expensive, despite excellent isolation efficiency of the protein A affinity chromatography, demands for developing alternative methods to the protein A affinity chromatography have increased.

Small polypeptide fragments that are specific to a constant region of an antibody have been introduced as an alternative to the protein A used in the conventional affinity chromatography. However, these polypeptide fragments contain six amino acids and are instable under a strong acid or base environment or at high temperature, and thus are not suitable for isolating high-concentration antibodies.

Thus, there is still a need to develop to methods of isolating an antibody and stable polypeptides that bind specifically to a constant region of an antibody when performing the isolation methods.

SUMMARY

Provided are a fusion protein that includes a polypeptide binding specifically to a constant region of an antibody and a stabilization protein linked to a terminal of the polypeptide, a polynucleotide encoding the fusion protein, and a cell including the polynucleotide.

Provided are a method of preparing the fusion protein, and a method of isolating an antibody by using the fusion protein.

Additional aspects will be set forth in part in the description which follows and, in part, will be apparent from the description, or may be learned by practice of the presented embodiments.

BRIEF DESCRIPTION OF THE DRAWINGS

These and/or other aspects will become apparent and more readily appreciated from the following description of the embodiments, taken in conjunction with the accompanying drawings of which.

DETAILED DESCRIPTION

Figure 1:
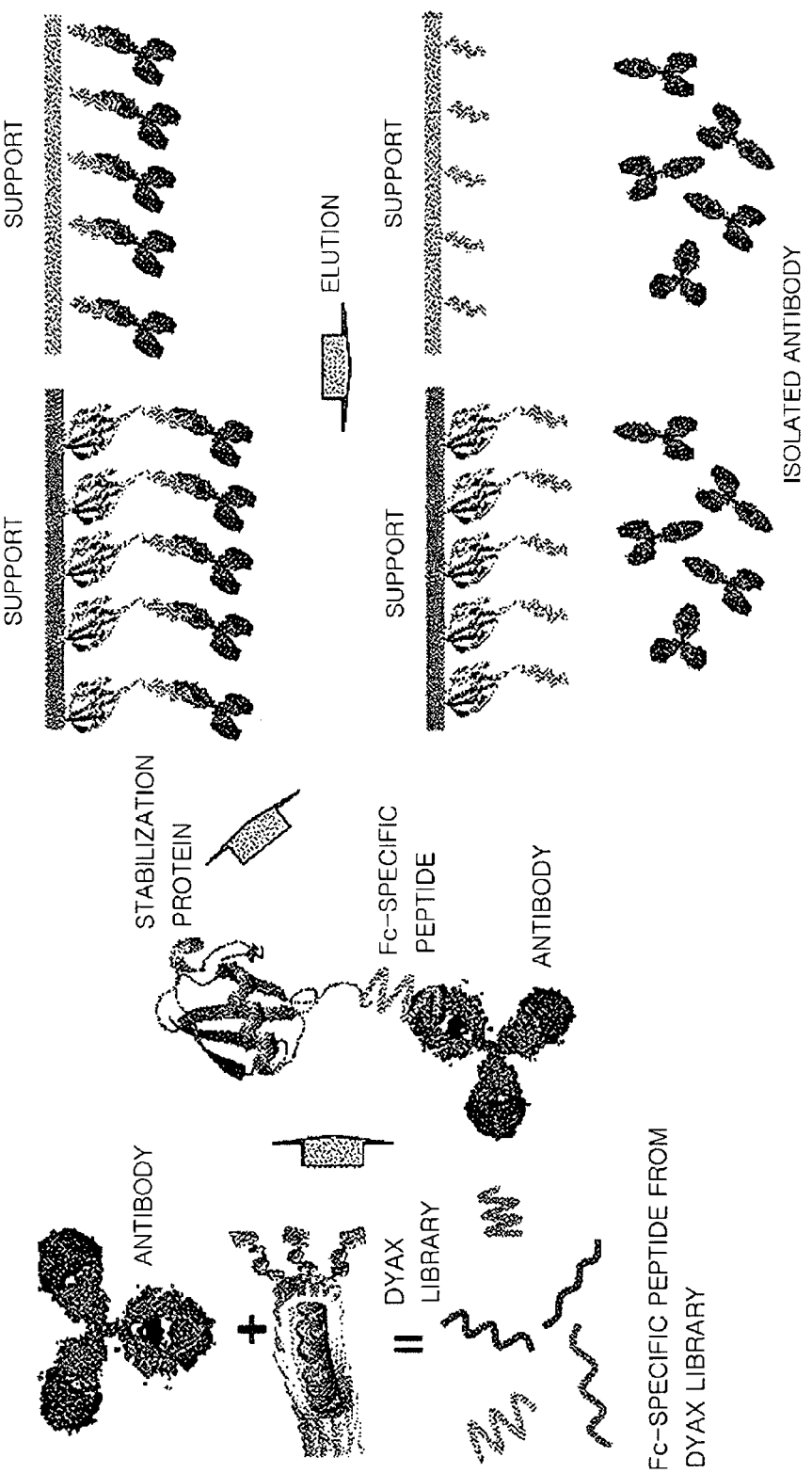
FIG. 1 is a schematic view illustrating a method of manufacturing a chromatography column for isolating an antibody and a method of isolating an antibody using the chromatography column, according to one or more embodiments of the present invention.

Reference will now be made in detail to embodiments, examples of which are illustrated in the accompanying drawings, wherein like reference numerals refer to the like elements throughout. In this regard, the present embodiments may have different forms and should not be construed as being limited to the descriptions set forth herein. Accordingly, the embodiments are merely described below, by referring to the figures, to explain aspects of the present description.

One or more embodiments of the present invention provide a fusion protein that includes a polypeptide binding specifically to a constant region of an antibody and a stabilization protein linked to a terminal of the polypeptide, a polynucleotide encoding the fusion protein, and a cell including the polynucleotide.

One or more embodiments of the present invention provide a method of preparing the fusion protein, and a method of isolating an antibody by using the fusion protein.

An embodiment of the present invention provides a fusion protein including a polypeptide binding specifically to a constant region of an antibody and a stabilization protein linked to a terminal of the polypeptide.

The antibody includes two full-length light chains and two full-length heavy chains, and each light chain is linked to the heavy chain by disulfide bonds. The antibody has constant regions including a heavy chain constant region and a light chain constant region. Heavy chain constant regions have gamma (γ), mu (μ), alpha (α), delta (δ) and epsilon (ε) type, and as a subclass, gamma 1(γ1), gamma 2(γ2), gamma 3(γ3), gamma 4(γ4), alpha 1(α1), and alpha 2(α2). Light chain constant regions have kappa (κ) and lambda (λ) type. The polypeptide that specifically binds to a constant region of an antibody refers to a polypeptide that binds to any amino acid or peptide contained in the heavy chain constant regions or the light chain constant regions. The term "polypeptide" refers to a linear polymer including two or more amino acids joined via peptide bonds.

The antibody may be selected from the group consisting of IgG, IgM, IgA, IgD, and IgE. For example, the antibody may be IgG.

In the fusion protein, the stabilization protein is fused with the terminal of the polypeptide that specifically binds to a constant region of an antibody. The stabilization protein may be fused with an N-terminal or C-terminal of the polypeptide that specifically binds to a constant region of an antibody. In the present specification, the term "stabilization protein" refers to a protein that is resistant to a condition under which a protein is denatured, for example, high temperature, or extremely high and low pHs. The stabilization protein may be selected from the group consisting of ubiquitin, ecotin, brazzein, 6-lactoglobulin, sakacin B, mxyn10, a small heat-stable acid-soluble protein of *Bacillus subtilis*, alkaline phosphatase, and recombinant monellin. For example, the stabilization protein may be ubiquitin.

Ubiquitin is a highly-conserved protein in the natural world and includes 76 amino acid sequences, and ubiquitins of evolutionary various species such as insects, trouts, and a human have perfect homology. In addition, ubiquitin is stable with respect to a change in pH, is not denatured even at high temperature, and is resistant to a protease. For example, ubiquitin may be human's wild-type or mutant-type ubiquitin of SEQ ID NO: 1 or SEQ ID NO: 2.

When the stabilization protein, for example, ubiquitin is fused with the polypeptide that specifically binds to a constant region of an antibody, the stability of the polypeptide may be improved. The polypeptide that specifically binds to a constant region of an antibody has a steric hindrance due to its relative small size. Thus, when a column is manufactured by binding the fusion protein to a support, the fusing with the ubiquitin may contribute to a decrease in the steric hindrance effect of the polypeptide, and thus excellent synergy effects can be obtained. According to an embodiment of the present invention, one or more stabilization protein may be fused with the terminal of the polypeptide.

Also, the stabilization protein may further have one or more Cys at a terminal thereof. According to the location of the stabilization protein with respect to the fusion protein, the one or more Cys may be included in an N-terminal or a C-terminal of the stabilization protein. For example, if the stabilization protein is fused with the C-terminal of the polypeptide, the one or more Cys may be included in the C-terminal of the stabilization protein. Since the one or more Cys is included in the fusion protein, when an affinity chromatography column is manufactured using the fusion protein, the fusion protein may easily bind to an activated support, for example, activated agarose beads.

The polypeptide included in the fusion protein may be selected from the group consisting of polypeptides having SEQ ID NO: 3 through SEQ ID NO: 6.

The fusion protein may bind to a support. The support may include a material selected from the group consisting of agar-agar; agarose; cellulose; cellulose ether such as hydroxypropyl cellulose or carboxymethyl cellulose; polyamide such as poly(meth)acrylamide; polyvinylalcohol; silica; and controlled porous glass, and may not be limited thereto. The support may have any shape. For example, the support may be selected from the group consisting of a support having a plurality of pillars on its surface, a support having a bead shape, and a support having a plurality of pores on its surface, that is, having a sieve structure. These supports may be used individually, or in a collection form, for example, a collection formed by filling a plurality of supports in a tube or vessel. The support may be used in a method of isolating an antibody. The method of isolating an antibody may be, for example, an affinity chromatography method. When the affinity chromatography method is used, the support may be filled in, for example, a cylindrical glass column.

The fusion protein may be attached to the support by a direct chemical reaction between the fusion protein and the support. Alternatively, a known appropriate reagent that binds the fusion protein to the support may be used to bind the fusion protein to the support by a known covalent bond. When the reagent is used, the support or the fusion protein is pre-activated by an activator. The activator may be, for example, epichlorohydrine; epibromohydrin; allyl-glycidylether; bisepoxide such as butanedioldiglycidylether; a halogen-substituted aliphatic compound such as dichloropropanol or divinylsulfone; carbonyldiimidazole; aldehyde such as glutar dialdehyde; quinone; cyanogen bromide; periodic acid such as sodium-meta-periodic acid; carbodimide; chlorotriazine such as cyanuric chloride; sulfonyl chloride such as tosyl chloride or tresyl chloride; N-hydroxy succine imide; 2-fluoro-1-methylpyridiniumtoluene-4-sulfonate; oxazolone; meleimide; pyridyl disulfide; or hydrazine, but is not limited thereto. The activator may be an epoxy compound such as epichlorohydrin, allyl-glycidine ether, or butandiol diglycidylether. The support to which the fusion protein binds may be a solid support, and the solid support may be selected from the group consisting of an agarose support, a dextrane-based support, a cellulose-based support, a organic synthesized polymer support, a controlled porous glass support, a silicate-based support, and a silica support, but is not limited thereto. For example, the solid support may be an agarose support.

Another embodiment of the present invention provides a polypeptide that binds specifically to a constant region of an antibody and is selected from the group consisting of polypeptides having SEQ ID NO: 3 through SEQ ID NO: 6.

Another embodiment of the present invention provides a polynucleotide encoding the fusion protein.

The term "polynucleotide" refers to a polymer of deoxyribonucleotide or ribonucleotide that exists in a single-stranded form or a double-stranded form. The term "polynucleotide" comprehensively includes a RNA genome sequence, cDNA, and a RNA sequence transcribed from a cDNA, and unless the context clearly indicates otherwise, includes an analogue of natural polynucleotide.

The polynucleotide may include, in addition to a nucleotide sequence encoding an amino acid sequence of the fusion protein, a complementary sequence to the nucleotide sequence. The complementary sequence may be a perfectly complementary sequence or a substantially complementary sequence to the nucleotide sequence. That is, the complementary sequence may be a sequence that is hybridized with, for example, a nucleotide sequence that encodes an amino acid sequence of the fusion protein under stringent conditions known in the art.

Meanwhile, a nucleotide sequence of the stabilization protein included in the fusion protein, for example, a nucleotide sequence of ubiquitin may be derived from mammals, for example, a human. In addition, the nucleotide sequence of ubiquitin may be any nucleotide sequence of ubiquitin that is searched for through a known nucleotide sequence search database, for example, NCBI Entrez (http://www.ncbi.nlm.nih.gov/Entrez/) or EMBL-EBI (http://www.ebi.ac.uk/). The polynucleotide may be a polynucleotide of SEQ ID NO: 7 or SEQ ID NO: 8.

Another embodiment of the present invention provides a recombinant vector including: the polynucleotide encoding the fusion protein that includes a polypeptide binding specifically to a constant region of an antibody and a stabilization protein linked to a terminal of the polypeptide; and a promoter operatively linked to the polynucleotide.

In the recombinant vector, the polynucleotide is operatively linked to the promoter. The term "operatively linked" means a functional linkage between a nucleotide expression regulating sequence (for example: promoter sequence) and another nucleotide sequence, wherein the nucleotide expression regulating sequence may regulate the transcription and/or translation of the other nucleotide sequences.

The recombinant vector may be an expression vector that stably expresses the fusion protein in a host cell. The expression vector may be a conventional vector that is used to express a foreign protein in plants, animals, or microorganisms in the art. The recombinant vector may be formed using various methods known in the art.

The recombinant vector may be constructed for use in prokaryotic or eukaryotic host cells. For example, if the recombinant vector is an expression vector and a prokaryotic cell is used as a host, the recombinant vector may include a strong promoter for transcription (for example, $p_L^\lambda$ promoter, trp promoter, lac promoter, tac promoter, T7 promoter etc.), a ribosome binding site for initiating translation, and a transcription/translation termination sequence. If a eukaryotic cell is used as a host cell, an origin of replication operating an eukaryotic cell included in a vector may be a f1 replication origin, a SV40 replication origin, a pMB1 replication origin, an adeno replication origin, an AAV replication origin, or a BBV replication origin, but is not limited thereto. The promoter used in the recombinant vector may be a promoter derived from a genome of a mammal cell (for example, metalthionine promoter) or a promoter derived from a virus of a mammal cell (for example, an adenovirus anaphase promoter, vaccinia virus 7.5K promoter, SV40 promoter, cytomegalo virus promoter, or tk promoter of HSV), and may in general include a polyadenylated sequence as a transcription termination sequence. The polynucleotide for expressing the fusion protein may be selected from the group consisting of polynucleotides of SEQ ID NO: 9 through SEQ ID NO: 12.

Another embodiment of the present invention provides a cell including the polynucleotide encoding the fusion protein that includes a polypeptide binding specifically to a constant region of an antibody and a stabilization protein linked to a terminal of the polypeptide.

The cell may be a cell that is transformed by the recombinant vector including the polynucleotide encoding the fusion protein that includes a polypeptide binding specifically to a constant region of an antibody and a stabilization protein linked to a terminal of the polypeptide and a promoter operatively linked to the polynucleotide.

That is, the cell may include the polynucleotide encoding the fusion protein that includes a polypeptide binding specifically to a constant region of an antibody and a stabilization protein linked to a terminal of the polypeptide in a genome of a host cell, or may include the recombinant vector including the polynucleotide sequence.

A host cell, which is capable of stably and consecutively cloning or expressing the recombinant vector, may be any host cell that is known in the art. Examples of the prokaryotic cell include *E. coli* JM109, *E. coli* BL21, *E. coli* RR1, *E. coli* LE392, *E. coli* B, *E. coli* X 1776, *E. coli* W3110, strains of *Bacillus* species such as *Bacillus subtillis* or *Bacillus thuringiensis*, and intestinal bacteria and strains such as *Salmonella typhymurium*, *Serratia marcescens*, or various *Pseudomonas* species. When transformation is performed using a eukaryotic cell, the eukaryotic cell may be *Saccharomyce cerevisiae*, an insect cell, a plant cell, or an animal cell. Examples of the eukaryotic cell include Sp2/0, Chinese hamster ovary (CHO) K1, CHO DG44, PER.C6, W138, BHK, COS-7, 293, HepG2, Huh7, 3T3, RIN, and MDCK cell lines.

The polynucleotide or the recombinant vector including the polynucleotide may be transferred to a host cell by using known methods. The method may vary according to a host cell. If the host cell is a prokaryotic cell, a $CaCl_2$ method and an electroporation method may be used. If the host cell is a eukaryotic cell, a microinjection method, a calcium phosphate precipitation method, an electroporation method, a liposome-mediated transfection method, or a gene bombardment method may be used. However, the method is not limited thereto.

The transformed host cell may be selected using a phenotype expressed by a selectable marker by well known methods in the art. For example, if the selectable marker is a specific antibiotic resistance gene, the transformant may be cultured in an antibiotic-containing medium.

Another embodiment of the present invention provides a method of preparing the fusion protein, wherein the method includes culturing a cell including the polynucleotide encoding the fusion protein that includes a polypeptide binding specifically to a constant region of an antibody and a stabilization protein linked to a terminal of the polypeptide, and obtaining a protein expressed in a culture.

Since the method according to the present embodiment is performed using the cell described above, the cell will not be described in detail herein.

The obtaining of the expressed fusion protein may be performed by, for example, affinity chromatography column, and a conventional purification method known in the art.

Another embodiment of the present invention provides a method of isolating an antibody, wherein the method includes forming a fusion protein-antibody complex by contacting the fusion protein with a sample containing an antibody; and isolating the antibody from the protein-antibody complex.

The isolation method according to the present embodiment will now be described in detail.

The fusion protein is contacted with a sample containing an antibody in order to form a protein-antibody complex.

The fusion protein may be a fusion protein prepared using the method of preparing a fusion protein. The fusion protein alone may be contacted with the sample. In addition, the fusion protein may be linked to a support. For example, an antibody may be contacted with an affinity chromatography column filled with a polypeptide that specifically binds to a constant region of an antibody. The affinity chromatography column has been described above. The sample may be any sample including an antibody. The antibody may be, for example, a monoclonal or polyclonal antibody of a human, a rabbit, a mouse, or a rat, but is not limited thereto. Meanwhile, the term "protein-antibody complex" may be a complex in which the polypeptide in the fusion protein binds specifically to a constant region of the antibody of the sample by a non-covalent bond.

Then, the antibody is isolated from the protein-antibody complex.

The protein-antibody complex may be formed by a non-covalent bond such as a hydrogen bond, an ionic bond, a hydrophobic interaction, or a van der Waals force. Thus, the protein and the antibody included in the protein-antibody complex may be separated from each other by, for example, changing a salt concentration of an effluent. The eluting of the antibody contained in the protein-antibody complex may be performed using known methods or methods modified therefrom. The isolated antibody may be subjected to a commercially available diafiltration device (for example, Amicon etc.) so that a salt contained therein may be removed from the antibody and the antibody is concentrated.

One or more embodiments of the present invention will be described in further detail with reference to the following examples. These examples are for illustrative purposes only and are not intended to limit the scope of the one or more embodiments of the present invention.

Example 1

Screening of Polypeptide that Binds Specifically to a Constant Region of an Antibody In order to obtain high specificity during screening using a peptide library, an antibody protein was immobilized on a plate with such an orientation that a constant region of the antibody protein was exposed.

Then, a phage peptide library (a polypeptide library having about 10-billion different amino acid sequences) produced by Dyax Co., Ltd. was added thereto in order to bind to the antibody protein, and the resultant was subjected to various binding hours and washing conditions. Then, peptide expression phages that bound with high affinity were selected.

In detail, a peptide library in which 19 amino acids were displayed on a surface of a phage was added to an antibody protein immobilized on a plate and then the resultant was washed under various conditions. Then, the bound phage was obtained by elution. The obtained phage was infected with *E. coli* and then amplified. Then, the phage was bound to the antibody protein, and then repeatedly subjected to more stringent washing conditions for a short reaction time in order to obtain a phage having a high bonding force, thereby obtaining a phage including a polypeptide that bound to a constant region of an antibody. The obtained phage was amplified, and then a phage plaque was selected and a genome DNA of the phage was isolated to identify a nucleotide sequence, thereby identifying the transcribed amino acid sequence of the polynucleotide binding to the constant region of the antibody.

Example 2

Preparation of Fusion Protein Including Polypeptide that Binds Specifically to a Constant Region of an Antibody and Ubiquitin In this experiment, a fusion protein was prepared by fusing ubiquitin with the polypeptide that binds specifically to a constant region of an antibody prepared according to Example 1.

A polynucleotide fragment encoding a fusion protein formed by fusing ubiquitin with a C-terminal of the polypeptide of Example 1 was obtained by PCR amplification using a human ubiquitin wild-type DNA and the polynucleotide of Example 1 as a template (SEQ ID NOS: 8 through 11). The polynucleotide fragment encoding a fusion protein was cloned into a pET21b (Novagen) vector and then expressed in *E. coli* BL21(DE3). In this regard, the culture used was an YT medium, and when an O.D. value was 0.6 at a wavelength of 600 nm, 1 mM IPTG (isopropyl-β-D-thiogalactopyranoside) was added thereto and then the resultant culture was incubated at a temperature of 37 for 4 hours. Cells obtained by the incubation were disrupted using a buffer including 50 mM Tris-HCl and 0.2 M NaCl at a pH of 8.0 by sonication, and then a centrifuge (10,000×g) was used to obtain a supernatant. The obtained supernatant was boiled at a temperature of 100 for 30 minutes and then a centrifuge (10,000×g) was used to obtain a supernatant. Then, 0.1N HCl was added to the obtained supernatant to reduce the pH to 3.0 and then the resultant was left for 10 minutes. Then, a centrifuge (10,000× g) was used to obtain a supernatant. The obtained supernatant was subjected to dialysis with a buffer containing 50 mM Tris-HCl and having pH of 8.0, and then to a resource Q column. The supernatant was washed with the buffer containing 50 mM Tris-HCl and having pH of 8.0, and then eluted with 0 to 500 mM NaCl concentration gradient. The obtained result was applied to a Superdex 75 column by using a buffer including 50 mM Tris-HCl and 0.2 M NaCl and having pH 8.0, thereby obtaining a purified fusion protein.

A test for analyzing a binding force of the fusion protein with respect to a constant region of an antibody was performed in the same manner as in Example 1. Among the polypeptides obtained according to Example 1 and the fusion proteins obtained according to the present experiment, all of which bind specifically to a constant region of an antibody, fusion proteins having a high binding force with respect to a constant region of an antibody were selected and the selected fusion proteins were used in Examples below.

Figure 2:
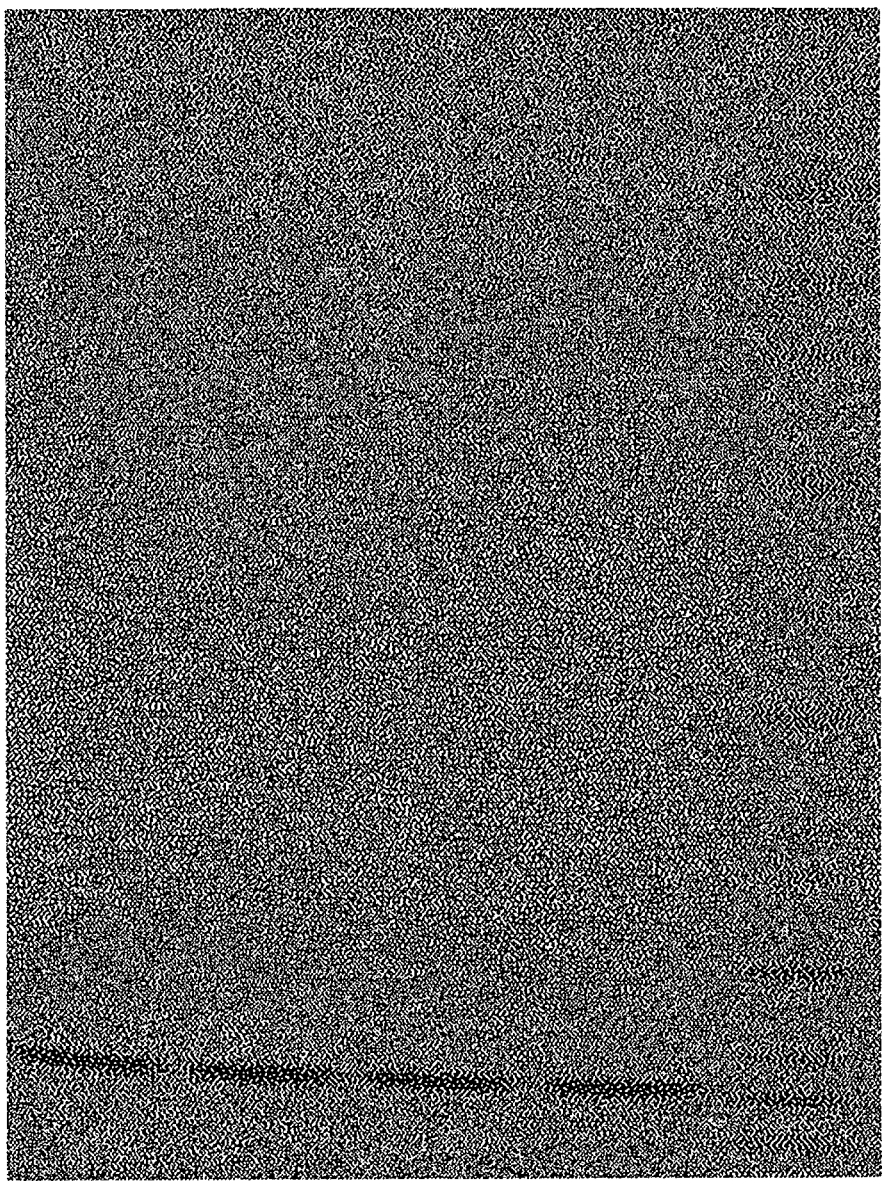
FIG. 2 shows results of sodium dodecyl sulfate polyacrylamide gel electrophoresis (SDS-PAGE) for evaluating the stability of a fusion protein that includes a polypeptide binding specifically to a constant region of an antibody and a stabilization protein linked to a terminal of the polypeptide with respect to pH or heat, according to one or more embodiments of the present invention, wherein lane 1 represents results for a wild-type fusion protein, lane 2 represents results for a fusion protein treated with 0.1 N HCl at a pH of 3 for 10 minutes; lane 3 represents results for a fusion protein treated with 1 mM NaOH at a pH of 11 for 10 minutes, lane 4 represents results for a fusion protein treated at a temperature of 100 for 30 minutes, and lane 5 represents results for a size marker.
Figure 3:
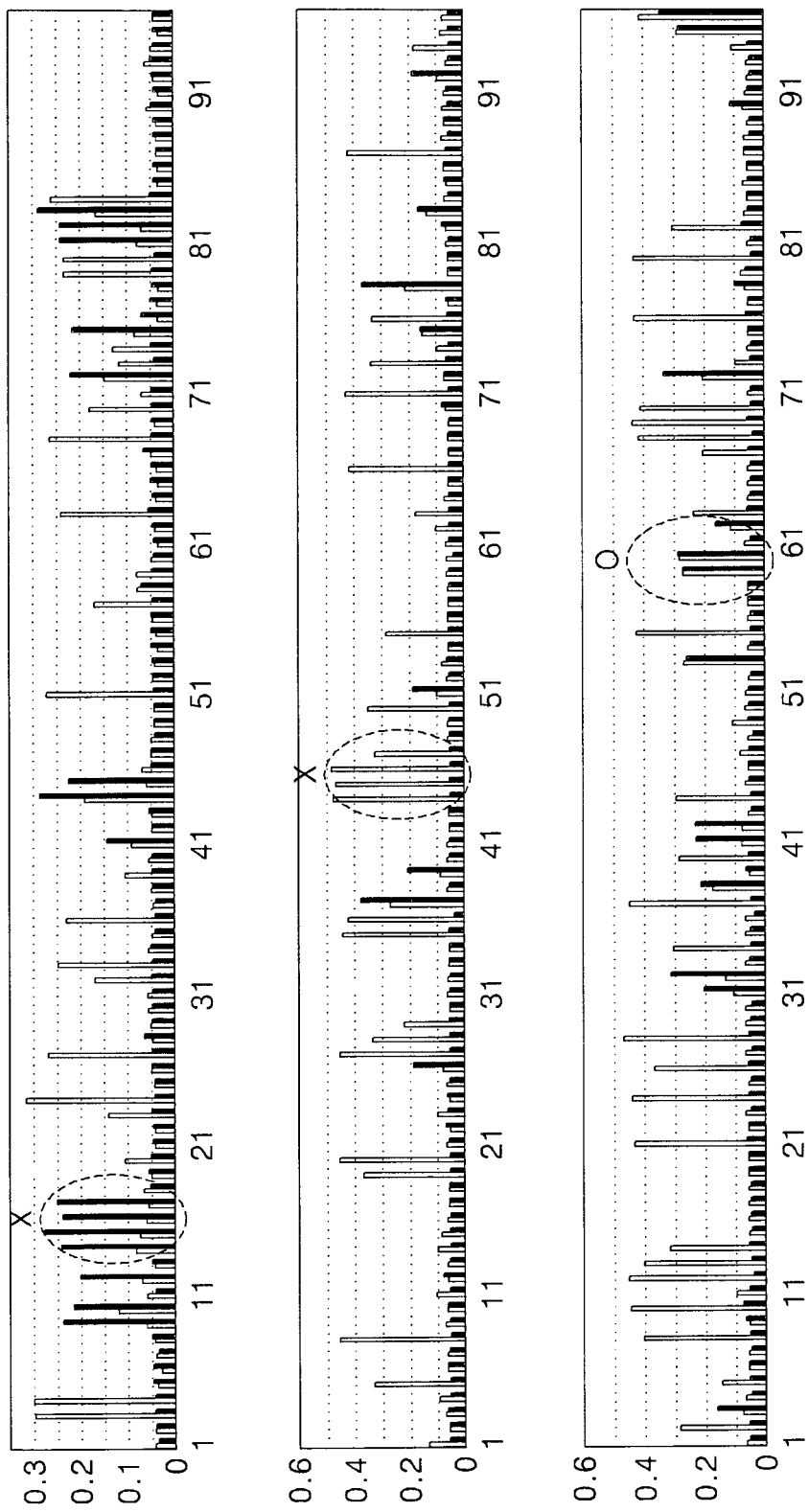
FIG. 3 shows selection of polypeptides binding specifically to a constant region of an antibody.

In addition, in order to evaluate stability of the obtained fusion protein according to pH or heat, the fusion protein was treated under an acid, a base, or at high temperature and then the result was identified by SDS-PAGE (FIG. 2). When treated with 0.1 N HCl having a pH of 3 (lane 2), treated with 1 mM NaOH having a pH of 11 for 10 minutes (lane 3), or heated at a temperature of 100 for 30 minutes (lane 4), the obtained fusion protein was not denatured. Thus, it can be seen that the fusion protein is very stable according to a pH and heat.

Example 3

Preparation of Chromatography Column for Isolating Antibody

Since in the fusion protein selected according to Example 2, a C-terminal of the fused ubiquitin contains a cysteine, the fusion protein was combined with a support by the cysteine, thereby producing a structure including a support and the fusion protein that are bound to each other by a covalent bond. A glass column was packed with the structure, thereby preparing an affinity chromatography column for isolating an antibody.

Example 4

Isolation of Antibody by Chromatography Column for Isolating Antibody

Herceptin, which is a monoclonal anti-Her2, was over-expressed in CHO cells. The supernatant of the obtained cell culture contained about 50 μM of an antibody. The pH of the supernatant of the obtained cell culture was adjusted by adding 1/10 volume of 1.0 M Tris-HCl(pH 8.0) thereto. Then, the supernatant of the obtained cell culture was loaded onto the chromatography column manufactured according to Example 3. Then, the chromatography column was washed with 50 mM Tris-HCl (pH 8.0)/0.5M NaCl in an amount 10 times greater than the volume of the chromatography column, and then washed with 50 mM sodium acetate (pH 5.6)/0.5M NaCl in an amount 10 times greater than the volume of the chromatography column. Then, the result was treated with 50 mM HCl to elute herceptin. Then, 1 M Tris-HCl (pH 9.0) was added thereto to adjust the pH of the result to be neutralized.

FIG. 1 is a schematic view illustrating a method of manufacturing a chromatography column for isolating an antibody and a method of isolating an antibody using the chromatography column, according to one or more embodiments of the present invention.

As described above, when a fusion protein that includes a polypeptide binding specifically to a constant region of an antibody and a stabilization protein linked to a terminal of the polypeptide, according to an embodiment of the present invention, and a method of isolating an antibody by using the fusion protein, according to an embodiment of the present invention, are used, an antibody may be efficiently isolated at low costs from a sample including the antibody.

It should be understood that the exemplary embodiments described therein should be considered in a descriptive sense only and not for purposes of limitation. Descriptions of features or aspects within each embodiment should typically be considered as available for other similar features or aspects in other embodiments.

What is claimed is:

1. A fusion protein comprising a polypeptide that specifically binds to a constant region of an antibody, and a stabilization protein, wherein the stabilization protein is ubiquitin, and wherein the polypeptide comprises the amino acid sequence of SEQ ID NO: 3.

2. The fusion protein of claim 1, wherein the ubiquitin comprises one or more terminal cysteine (Cys) residues.

3. The fusion protein of claim 1, wherein the fusion protein is bound to a support.

4. A method of preparing a fusion protein, the method comprising: culturing a host cell comprising a polynucleotide encoding the fusion protein of claim 1; and obtaining the fusion protein expressed in the cultured host cell.

5. A method of isolating an antibody, the method comprising:

forming a fusion protein-antibody complex by contacting a fusion protein of claim 1 with a sample containing an antibody; and isolating the antibody from the protein-antibody complex.

6. The method of claim 5, wherein the ubiquitin comprises one or more terminal cysteine (Cys) residues.

7. The method of claim 5, wherein the fusion protein is bound to a support.

8. The method of claim 7, wherein the support is a solid support.

9. The method of claim 8, wherein the solid support is selected from the group consisting of an agarose support, a dextrane-based support, a cellulose based support, a organic synthesized polymer support, a porous glass support, a silicate-based support, and a silica support.

10. The method of claim 7, wherein the support comprises a material selected from the group consisting of agar-agar, agarose, cellulose, cellulose ether, polyamide, polyvinylalcohol, silica, and porous glass.

11. The method of claim 10, wherein the cellulose ether is hydroxypropyl cellulose or carboxymethyl cellulose.

12. The method of claim 10, wherein the polyamide is poly(meth)acrylamide.

* * * * *